United States Patent [19]

Juncosa

[11] Patent Number: 4,862,092

[45] Date of Patent: Aug. 29, 1989

[54] APPARATUS AND METHOD FOR IN VITRO DETECTION OF ABNORMAL TISSUES

[75] Inventor: Robert D. Juncosa, Santa Ana, Calif.

[73] Assignee: American Mediscan, Inc., Los Angeles, Calif.

[21] Appl. No.: 892,301

[22] Filed: Aug. 4, 1986

[51] Int. Cl.[4] ............................................. G01N 27/28
[52] U.S. Cl. .................................. 324/450; 324/61 P; 324/65 P
[58] Field of Search ............................... 324/444–450, 324/61 P, 65 P, 376; 128/734, 749

[56] References Cited

U.S. PATENT DOCUMENTS

| | | | |
|---|---|---|---|
| Re. 31,333 | 8/1983 | Barben | 324/450 |
| 2,942,176 | 6/1960 | Brownscombe | 324/376 |
| 3,302,101 | 1/1967 | Glanville | 324/376 |
| 4,498,481 | 2/1985 | Lemke | 128/734 |
| 4,540,002 | 9/1985 | Atlas | 128/734 |
| 4,646,000 | 2/1987 | Wills | 324/376 |

Primary Examiner—Reinhard J. Eisenzopf
Assistant Examiner—Jose M. Solis
Attorney, Agent, or Firm—George J. Netter

[57] ABSTRACT

A tissue testing chamber having a hollow, electrically insulative housing separable into two parts or halves, each half including a plate-like working electrode and spaced therefrom an annular measuring electrode, with electrical leads provided to each of the electrodes for interconnection with external control and measuring equipment. Each housing half or test chamber half has a cavity communicating with both the working and measuring electrodes and an open end. The housing halves clamp the test specimen between them. A quantity of Ringer's solution is added to each housing cavity and the four electrodes are then connected in a four electrode impedance bridge with selectively variable impedances (e.g., capacitance) which on bridge balance provides capacitance of specimen.

12 Claims, 2 Drawing Sheets

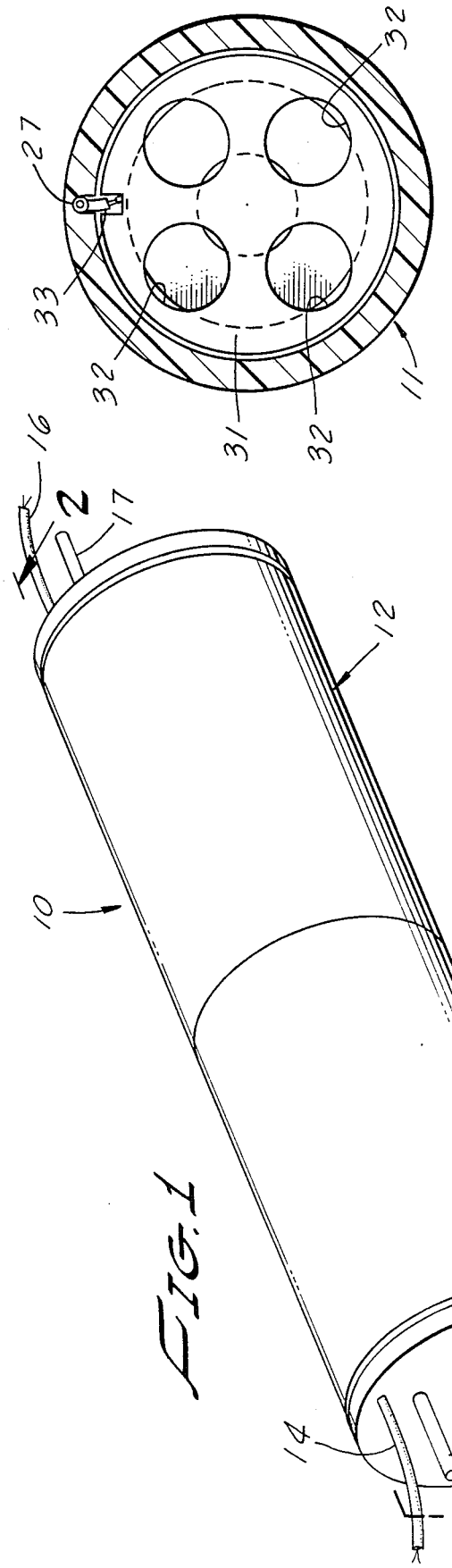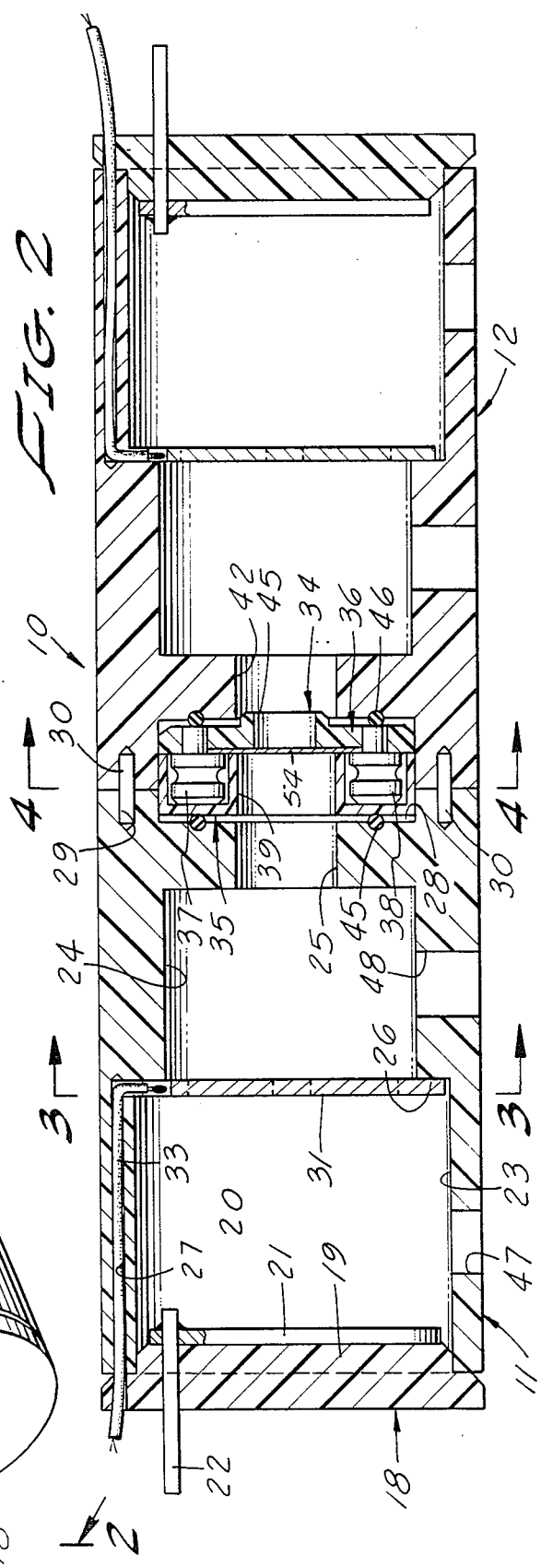

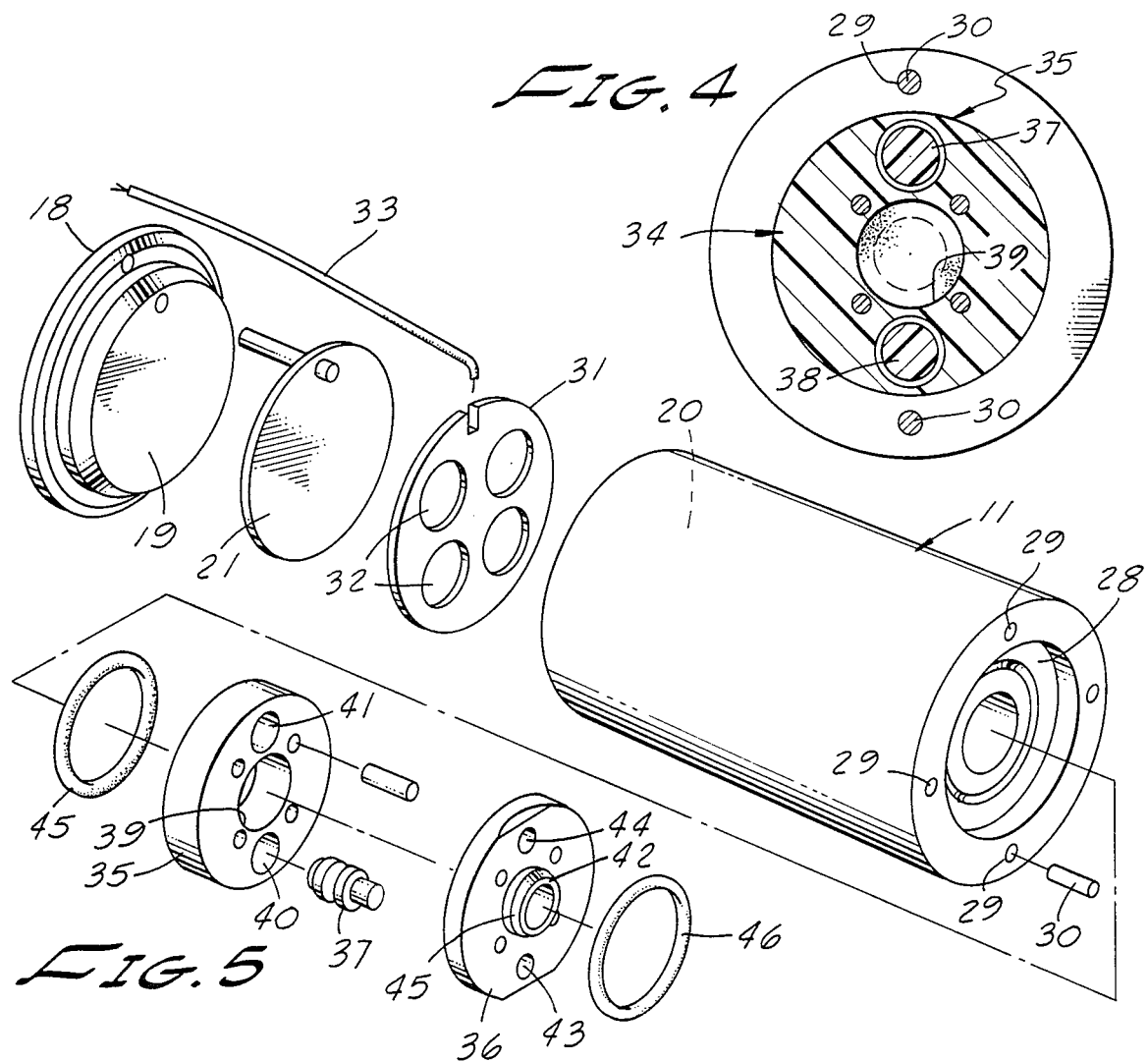
FIG. 4
FIG. 5
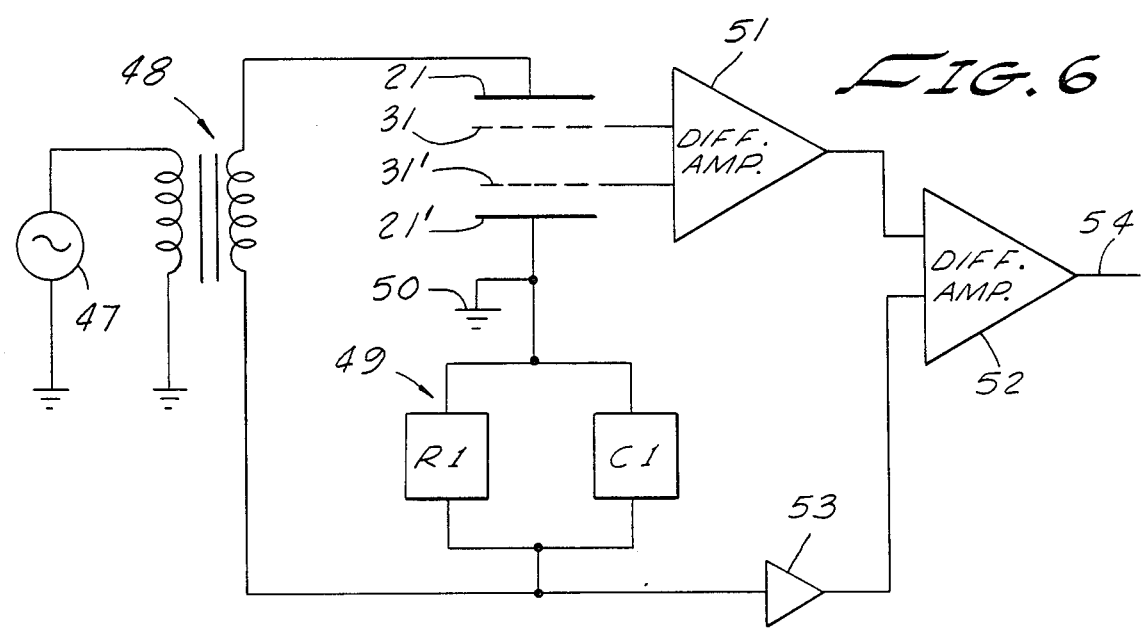
FIG. 6

APPARATUS AND METHOD FOR IN VITRO DETECTION OF ABNORMAL TISSUES

The present invention pertains generally to the in vitro examination of tissues and, more particularly, to apparatus and method for the detection of abnormal tissues and early indication that a tissue will become abnormal.

BACKGROUND OF THE INVENTION

As used herein the term "abnormal tissue" refers to all tissues which have undergone malignant induction such that they may eventually exhibit loss of growth control which is frequently referred to as cancerous or tumorous growth. The detection of the presence of such abnormal tissues is often made difficult because they are located within the body so that until discomfort or other symptoms are experienced by the individual, the existence of the abnormal tissues may not even be suspected. Additionally, present day procedures for early detection can be so expensive and complex as to make their use restricted. Therefore, it would be high advantageous to be able to detect quickly and simply the presence of abnormal tissue, or, ideally, the eventuality of abnormal tissue growth within a body cavity of the host, for example, and preferably the technique should be minimally invasive.

Many forms of cancers or tumors require extended periods of time to achieve a size detectable or injurious to the host, and in some cases this may even take many years. Treatment at this time is considerably more effective when the abnormal tissues are in their early phases and long before they have achieved growth sufficient to cause discomfort or produce detectable symptoms. It would, therefore, also be advantageous to be able to detect the presence of abnormal tissues in their early phases or, even earlier, to detect the tendency for tissues to become abnormal.

Several research efforts have been directed toward discovering the relationship between the electrical impedance of biological tissues and its condition or health. For example, U.S. Pat. No. 3,949,736 discloses that the impedance of biological tissues can provide a useful indication as to whether tissues are healthy or diseased. Specifically, this patent suggests that changes in impedance of biological tissues can be used as a technique for diagnosis of certain carcinomas. According to this patented technique, a low level electric current is passed through the investigated tissue with measurement of the voltage drop across the tissue providing an indirect indication of the overall tissue impedance (i.e., resistance and capacitance). Also, according to this patent, increase in the impedance of the tissue is associated with an abnormal condition of the cells composing the tissue and indicative of a tumor, carcinoma, or other abnormal biological condition of the tissue.

In U.S. Pat. No. 4,729,385 entitled "Probe and Method of Use for Detecting Abnormal Tissues" by R. Juncosa and R. Davies, assigned to the same assignee as the present patent, a special probe is located immediately adjacent to the tissue to be examined (e.g., in the colon) and a second probe is brought into contact with the subject at some other point. The two probes are then incorporated into a bridge circuit and the electrical resistance and capacitance of the examined tissue is determined. It is a fundamental principle of this invention that the tissue capacitance has a direct relationship to the biological condition of the tissue and, more particularly, the capacitance of healthy tissues is substantially greater than that of tissues which are eventually found to develop tumors. The apparatus and techniques disclosed in this prior patent are essentially designed for in vivo use with the specific design of the probes being such that they can be coupled with an endoscope (i.e., colonoscope or other such apparatus) for introduction into an epithelial cavity and thereby locate a measuring probe closely adjacent tissues to be examined.

There are many situations and circumstances where it is neither advisable nor practicable to make direct measurements on the patient itself, but rather instead to take tissue samples which are examined in a labororatory, for example.

SUMMARY OF THE DISCLOSURE

It is therefore a primary aim and object to provide an apparatus and method for determining the resistance and capacitance of a tissue specimen as a diagnostic indication of either the existence or a tendency towards tumerous or cancerous growth of the tissue.

The tissue testing chamber consists of a hollow, electrically insulative housing which is separable into two parts or halves, each half including a plate-like working electrode and spaced therefrom a foraminous plate measuring electrode, with electrical leads provided to each of the electrodes for interconnection with external control and measuring equipment. Each housing half or test chamber half has a cavity communicating with both the working and measuring electrodes and an open end.

In use, the open ends of the two housing halves are fit together with the test specimen clamped therebetween. A quantity of a suitable solution (e.g., Ringer's solution) is added to each housing cavity and the four electrodes are then connected in a four-arm impedance bridge with selectively variable impedances (e.g., resistance and capacitance). On bridge balance, the impedance of the tissue specimen is determined as a function of the reduced current through a differential amplifier. This latter aspect is important due to the fact that biological tissues consist of semi-solids and liquids which act as electrolytes, and the interface between an electrode and the electrolyte results in an electrode polarization impedance when an electric current passes therethrough, which polarization impedance can be of sufficient magnitude to introduce a substantial error into the desired impedance determination.

DESCRIPTION OF THE DRAWINGS

FIG. 1 is a perspective view of an abnormal tissue testing chamber in accordance with the present invention.

FIG. 2 is a side elevational, sectional view of the testing chamber of FIG. 1 taken along the line 2—2 of FIG. 1.

FIG. 3 is an end elevational, sectional view taken along line 3—3 of FIG. 2 through the measuring electrode.

FIG. 4 is a further end elevational view along line 4—4 of FIG. 2.

FIG. 5 is an exploded view of the chamber of FIG. 1 showing its component parts.

FIG. 6 is a function block electrical circuit schematic of equipment for measuring tissue impedance with the described apparatus.

DESCRIPTION OF A PREFERRED EMBODIMENT

The fundamental theory of operation of the present invention is the same as that of the referenced prior patent, namely, that the magnitude of the electrical capacitance of biological tissues provides a direct indication as to the health or diseased condition of these tissues. Specifically, it can be shown that the capacitance of healthy tissues is substantially greater than that of cancerous tissues. In addition, it is a basic premise of this invention that the capacitance of tissues which are presently analyzable as healthy but which, in fact, in the future will develop into tumors or carcinomas is also substantially lower than healthy tissues. Accordingly, it is an important aspect of the described apparatus to be able to examine tissues and determine not only their present status as to being healthy or diseased but, also, provide an early indication of tissues which are tending towards and will become tumors or carcinomas in the future. Moreover, the apparatus and techniques to be described herein are applicable for the testing of tissues in vitro as opposed to in vivo examination of a patient's tissues.

Turning now to the drawing and particular FIG. 1, the tissue testing device of this application is identified generally as 10 and is seen to consist of two generally cylindrical parts 11 and 12 which are separable, and, in use, clamp a sample of tissue (not shown) to be examined therebetween. Four lead wires 14 through 17 have one end each interconnected with internally located electrodes to be described and are externally interconnected with measuring and control equipment to effect capacitance measurement of the tissue sample or specimen.

With reference to FIGS. 2 and 3, as already noted the device 10 consists of the separable parts 11 and 12 which are substantially identical to one another both as to component parts and in the detailed construction of the various parts. Accordingly, the description of the detailed construction of only the part 11 will be given with it being assumed that the second part 12 is constructed in the same manner except for certain indicated differences.

The overall tissue measuring chamber part 11 is cylindrical in form and includes at its outer end a disc-like end cap 18 the outer part having a diameter substantially the same as that of the part 11 and an inner part 19 of diameter enabling ready fit within the cavity 20 of part 11. The end cap is preferably constructed of a moldable or machineable acrylic plastic which is rigid, electrically insulative and not readily deformable under relatively great temperature extremes.

A disc-like metal electrode 21, which will be referred to hereinafter as a working electrode, includes an elongated pin or rod 22 conductively connected to an edge portion of the electrode. Preferably, the electrode and pin are constructed of a metal which is an excellent electrical conductor such as silver coated with silver chloride, for example. The electrode 21 is contemplated for assembly onto the end cap inner part 19 with the pin 22 passing through the end cap. The diameter of the electrode 21 is less than that of the inner diameter of the cavity 20 leaving an outer annular space therebetween when the electrode and end cap are assembled together.

The chamber part 11 includes a generally cylindrical body of uniform outer diameter identical to the outer diameter of end cap 18. The chamber part cavity 20 has a first diameter portion 23 substantially identical to that of end cap inner part 19, a second smaller diameter portion 24 in open communication with portion 23, and a relatively small diameter opening 25 in the chamber part end wall. The two different diameter portions 23 and 24 are separated by an internal shoulder 26. Moreover, a passageway 27 extends along the chamber part wall, one end exiting internally adjacent the shoulder 26 and the other end at the end edge of the part wall to align with a further opening in end cap 18.

The outer end wall of the chamber part 11 includes a cylindrical cavity 28 concentric with and larger than opening 25. Additionally, the same outer end wall includes several openings 29 which can be aligned with openings 29 in part enabling the parts to be aligned and secured together by pins 30.

A further metal disc electrode 31 hereinafter referred to as a measuring electrode, has a diameter such as to enable fitting receipt within the chamber part large diameter portion 23 for fixed location against shoulder 26 (FIGS. 2 and 3). The measuring electrode includes several openings 32 extending therethrough and an edge connected lead wire or pin 33 which is threaded through passageway 27 and outwardly of end cap 18. Preferably the electrode 31 is constructed of the same materials as working electrode 21.

When the two chamber parts 11 and 12 are endconnected by pins 30, the cavities 28 of each chamber part are aligned and form a single large cavity which, during use, receives a tissue holder 34. With reference to both FIGS. 2 and 5, the tissue holder is seen to include a first wall member 35, a second wall member 36, and locking plugs 37 and 38 which fit together, in use, to secure a tissue specimen therebetween.

The first wall member 35 is a disk shaped body constructed of an insulative material and having an outer diameter enabling sliding receipt within the cavity 28 (FIG. 2). In addition to an axial opening 39 which passes completely through the first wall member, there are two further openings 40 and 41 which only extend partially through the wall member and open outwardly on the same member side.

The second wall member 36 is also disc shaped with an outer diameter the same as that of the first wall member. A central opening 42 extends through the wall member as well as two further openings 43 and 44. Hub 45 surrounds the central opening 42 on the surface which faces away from the first wall in assembly of the parts.

The locking plugs 37 and 38 each have a smoothly uniform end which is fittingly received within openings 43 and 44, and an outer larger diameter portion with at least two flanges thereon of such diameter as to enable loose fitting within the first wall member openings 40 and 41.

In use of the tissue container, a tissue specimen 54 of transverse dimension greater than openings 39 and 42 is located over the face of wall member 35 and by use of plugs 37, 38 the second wall member is clamped thereover (FIG. 2). O-rings 45 and 46 are located within the cavities 28, one at each side of the tissue container, and when the chamber parts 11 and 12 are secured about the container, these O-rings prevent leakage of fluids from one chamber part to the other.

With the specimen mounted in the container between the parts 11 and 12 as described, the cylindrical parts are then filled with a liquid through openings 47 and 48 known as Ringer's solution (in mM: Na, 140; K, 5.2; Ca, 1.2; Mg, 1.2; HCO3, 25; HPO4, 2.4; HPO4, 0.4; Cl, 119.8; glucose, 10). Alternatively, chlorine salts of bicarbonate and chloride can be used to replace Na, if desired.

For a detailed presentation of electronic apparatus to effect capacitance measurement of a tissue sample held by the described device 10, reference is made to the referenced prior patent; however, this measurement technique is depicted generally in FIG. 6. As shown there, a selectively variable oscillator 47 applies energizing voltage over an extended frequency range (e.g., 10 Hz—7 kHz) to a transformer 48. The transformer secondary is connected across a series circuit consisting of working electrode 21, measuring electrode 31, the measuring electrode 31' of device part 12, working electrode 21' of part 12, and a parallel circuit 49 of selectively adjustable capacitance (C1) and resistance (R1). The interconnection lead between working electrode 21' and R1/C1 parallel circuit 49 is fed through a balancing amplifier 40 to form a second input to differential amplifier 53. The signal at 40 represents an "error" between the present value of "R1/C1" and the tissue impedance, which error signal is used to adjust the "R1/C1" value in a direction bringing the error signal to zero. At this time, the tissue capacitance closely approximates the final adjusted value of "C1" in the parallel circuit 36. In the electrical apparatus described in the referenced prior patent, the changes in adjustment of the "R1/C1" values are under the control of a microprocessor. Finally, the measured values of tissue capacitance can be either printed out or otherwise displayed. Still further, presently measured capacitance can be compared against normal and abnormal reference data stored in lock-up tables, for example, so that read-out can give a direct indication of the tissue specimen health.

What is claimed is:

1. Apparatus for use in measuring epithelial tissue impedance, comprising:
    first and second insulative chambers each having a closed end wall and an opening in the opposite end wall;
    a pair of first platelike electrodes respectively mounted within the insulative chambers closely adjacent the inner surface of the closed end wall of each chamber;
    a pair of second platelike electrodes having at least one opening therein respectively mounted within the insulative chambers spaced from said first platelike electrode toward the open end wall;
    means for interfitting the insulative chambers open end walls together in fluid sealing relation and for simultaneously securing a tissue specimen between the open end walls of the first and second insulative chambers; and
    separate means conductively secured to each electrode and extending to the outside of the chambers for connection to electrical impedance measuring equipment.

2. Apparatus as in claim 1, in which each chamber closed end wall is removable and the respective first platelike electrode is secured thereto.

3. Apparatus as in claim 1, in which the platelike electrodes are constructed of silver coated with silver chloride.

4. Apparatus as in claim 1, in which the insulative chambers are constructed of polyethylene.

5. Apparatus as in claim 1, in which the first platelike electrode includes an imperforate metal disc and the interconnection means includes a metal rod having an end portion silver soldered to the metal disc.

6. Apparatus as in claim 1, in which the chambers additionally include selectively closable openings via which liquid electrolyte can be added and removed to the interior of the chambers while the open ends of said chambers are sealingly related to one another.

7. Apparatus as in claim 1, in which the interfitting means includes first and second disc shaped bodies each having a central opening, and locking plug means for releasably securing the first and second disc shaped bodies together, said bodies each being respectively located within a cavity in the open end of the first and second chambers.

8. Apparatus as in claim 7, in which there is further provided an O-ring sealingly located between an outer surface of each disc shaped body and the chamber cavity within which the said disc shaped body is received.

9. Apparatus as in claim 1, in which the outer end walls of the chambers include aligned openings and pins within said aligned openings for releasably securing the chambers together.

10. Apparatus as in claim 8, in which the outer end walls of the chambers have aligned openings and pins in said openings for securing the chamber end walls together and contain the first and second disc shaped bodies within the chamber cavities.

11. Apparatus as in claim 8, in which the first and second disc shaped bodies are constructed of acrylic.

12. Apparatus as in claim 7, in which the locking plug means includes a pair of plugs each having a uniformly smooth end portion and at least two spaced apart enlarged flanges.

* * * * *